United States Patent [19]

Hasofer

[11] Patent Number: 4,754,747

[45] Date of Patent: Jul. 5, 1988

[54] TREATMENT OF COLIC IN INFANTS

[76] Inventor: Baruch M. Hasofer, 159 Orrong Road, East St. Kilda, 3183, Victoria, Australia

[21] Appl. No.: 94,989

[22] Filed: Sep. 10, 1987

[51] Int. Cl.[4] .............................................. A61H 1/00
[52] U.S. Cl. .................................... 128/24 R; 128/67; 280/47.38
[58] Field of Search ................ 128/67, 1 B, 1 C, 68 R, 128/68, 69, 70, 78, 44; 5/105, 108, 109, 446; 280/47.38, 47.41, 47.4

[56] References Cited

U.S. PATENT DOCUMENTS

| | | | |
|---|---|---|---|
| 1,815,952 | 7/1931 | Morriss | 280/47.38 |
| 2,281,629 | 5/1942 | Snow | 5/1 |
| 2,971,796 | 2/1961 | Morval et al. | 280/47.38 |
| 3,529,590 | 9/1970 | Grosholz | 128/1 B |
| 3,564,626 | 2/1971 | Nelson | 280/47.38 |
| 4,590,631 | 5/1986 | Varney | 128/33 |
| 4,648,142 | 3/1987 | Bruning | 5/62 |
| 4,681,096 | 7/1987 | Cuervo | 128/33 |

*Primary Examiner*—Edgar S. Burr
*Assistant Examiner*—Huong Q. Pham
*Attorney, Agent, or Firm*—Sughrue, Mion, Zinn, Macpeak, and Seas

[57] ABSTRACT

A device for the treatment of colic in infants comprises a resiliently compressible body in the form of a fabric tube containing a plastics foam. The body is attached to the mattress of a baby carriage by means of a strap. When a baby is placed face down on the mattress, with its stomach against the body, forward and backward movement of the carriage will cause the body to gently massage the stomach to alleviate colic symptoms.

6 Claims, 1 Drawing Sheet

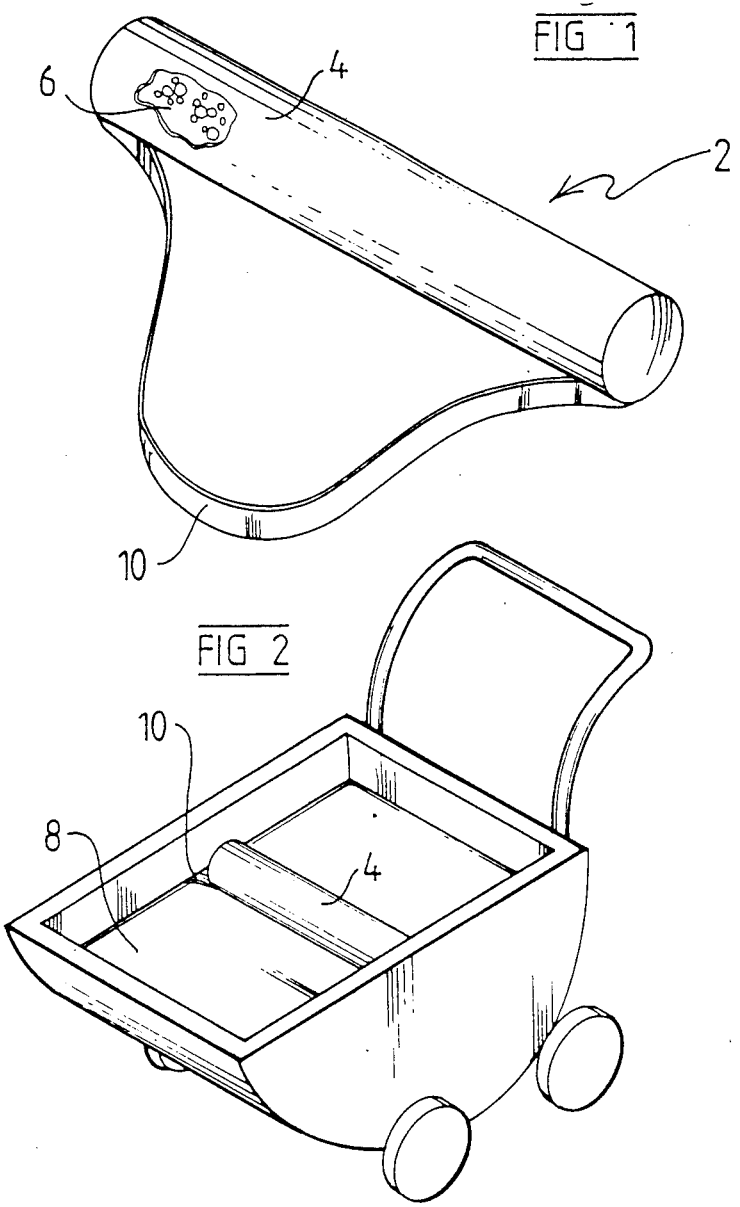

TREATMENT OF COLIC IN INFANTS

FIELD OF THE INVENTION

The invention relates to the treatment of colic in infants. In particular it relates to a device for aiding the expulsion of wind from an infant's abdomen.

DESCRIPTION OF THE PRIOR ART

Discomfort from wind or colic results from infants swallowing air during feeding or from disturbances in the digestive process.

In the past, colic has been alleviated by picking the infant up, holding its head over the shoulder with the baby's stomach against the shoulder and gently massaging the infant's back until the infant dispels any accumulated wind or until the discomfort is alleviated.

An object of the invention is to provide a device for facilitating the treatment of colic symptoms without the need to hold the infant.

SUMMARY OF THE INVENTION

According to the present invention, there is provided a device for alleviating colic in an infant, comprising means defining an elongate resiliently compressible body, and means for attaching the body to a mattress of a baby carriage so as to extend transversely of the mattress whereby when a baby is placed face down on the mattress with its stomach against the body and the carriage is moved backwards and forwards the body will gently massage the stomach to alleviate colic.

Further according to the invention, there is provided a baby carriage including a mattress and a resiliently compressible elongate body extending transversely of the upper surface of the mattress in a position to support the stomach of a baby placed face down onto the mattress, the body acting to gently massage the stomach when the carriage is rolled forward and backward so as to alleviate colic symptoms.

Still further according to the invention, there is provided a method of alleviating colic symptoms in an infant, comprising providing a wheeled baby carriage having a mattress, providing the mattress with a resiliently compressible body extending transversely of the mattress in a position to support the baby's stomach, placing a baby face down on the mattress with its stomach resting on the body, and moving the carriage backward and forward to cause the body to gently massage the stomach and thereby alleviate colic symptoms.

BRIEF DESCRIPTION OF THE DRAWINGS

An embodiment of the invention will now be described, by way of example only, with reference to the accompanying drawings, in which:

FIG. 1 is a perspective view of a massaging device in accordance with the invention; and FIG. 2 is a perspective view showing the device installed on a mattress in a baby carriage.

DESCRIPTION OF THE PREFERRED EMBODIMENT

As shown in the drawings, a massaging device for the treatment of colic in infants comprises an elongate cylindrical body 2 which is able to resiliently deform under the weight of an infant, and means for attaching the body to the mattress of a baby's pram or other wheeled baby carriage.

In the preferred embodiment, the cylindrical body 2 is defined by a closed outer tube 4 filled with a resiliently compressible stuffing 6, such as a resilient plastic foam, which is preferred although other materials may be used. Preferably, the outer tube is of a fabric and the overall construction is such that the device is washable.

To attach the device to the mattress 8 of a pram or other baby carriage, a strap 10 is attached to each end portion of the body. Preferably, the strap 10 is a one-piece elastic strap which is placed under tension around the mattress 8, as shown in FIG. 2. Alternatively, other attachment means such as a two-part touch and close fastener as sold under the registered Trade Mark "Velcro" may be used.

In alternative forms of the invention, the body 2 may be defined by a tubular inflatable bladder and the body 2 may be permanently attached to the mattress 8.

To use the device, the body 2 is placed on top of the mattress, in a position to lie beneath the baby's stomach, the body being fastened in position by stretching the elastic strap 10 around the mattress 8. The mattress 8 is placed in the pram or other baby carriage and the baby is then placed face-down on the mattress with his stomach resting on the resilient body. Gentle forward and backward motions of the pram for a few minutes will cause the resilient body to gently massage the stomach which assists in alleviating colic and relaxing the baby who will usually fall asleep during the action.

The device has been found effective for infants up to about six (6) months old. The embodiment has been described by way of example only and modifications are possible within the scope and spirit of the invention.

I claim:

1. In combination, a baby carriage including a mattress and a resiliently compressible elongate body extending transversely of and projecting above the upper surface of the mattress in a position to support the stomach of a baby placed face down onto the mattress, the body acting to gently massage the stomach when the carriage is rolled forward and backward so as to alleviate colic symptoms.

2. A device according to claim 1, wherein the body comprises an outer tube filled with a resilient material.

3. A device according to claim 2, wherein the outer tube is a fabric and the filling consists of a resilient foam.

4. A device according to claim 1, wherein the attachment means comprises a strap attached to the body, such that the body and strap surround the mattress.

5. The combination according to claim 1, further comprising means for releasably attaching the body to the mattress.

6. A method of alleviating colic symptoms in an infant comprising providing a wheeled baby carriage having a mattress, providing the mattress with a resiliently compressible body extending transversely of and projecting above the mattress in a position to support the baby's stomach, placing a baby face down on the mattress with its stomach resting on the body, and moving the carriage backward and forward to cause the body to gently massage the stomach and thereby alleviate colic symptoms.